United States Patent
Pan et al.

(10) Patent No.: US 11,619,602 B2
(45) Date of Patent: Apr. 4, 2023

(54) THREE-DIMENSIONAL HYDROGEL-GRAPHENE-BASED BIOSENSOR AND PREPARATION METHOD THEREOF

(71) Applicant: HARBIN INSTITUTE OF TECHNOLOGY, Heilongjiang (CN)

(72) Inventors: Yunlu Pan, Heilongjiang (CN); Zhuang Hao, Heilongjiang (CN); Xuezeng Zhao, Heilongjiang (CN)

(73) Assignee: HARBIN INSTITUTE OF TECHNOLOGY, Heilongjiang (CN)

( * ) Notice: Subject to any disclaimer, the term of this patent is extended or adjusted under 35 U.S.C. 154(b) by 0 days.

(21) Appl. No.: 17/878,593

(22) Filed: Aug. 1, 2022

(65) Prior Publication Data
US 2022/0404301 A1 Dec. 22, 2022

Related U.S. Application Data

(63) Continuation of application No. PCT/CN2021/103609, filed on Jun. 30, 2021.

(30) Foreign Application Priority Data

Jun. 17, 2021 (CN) .......................... 202110672440.1

(51) Int. Cl.
*G01N 27/04* (2006.01)
*C01B 32/194* (2017.01)
(Continued)

(52) U.S. Cl.
CPC ............ *G01N 27/04* (2013.01); *C01B 32/194* (2017.08); *C08F 220/56* (2013.01); *G01N 27/02* (2013.01);
(Continued)

(58) Field of Classification Search
CPC ........ G01N 27/04; G01N 27/02; G01N 33/48; G01N 33/50; G01N 33/5438;
(Continued)

(56) References Cited

U.S. PATENT DOCUMENTS

2017/0307562 A1* 10/2017 Goldsmith ........... C12Q 1/6869
2017/0350882 A1* 12/2017 Lin .................. G01N 33/54353

FOREIGN PATENT DOCUMENTS

| CN | 1733935 A | 2/2006 |
|---|---|---|
| CN | 108107144 A | 6/2018 |

(Continued)

OTHER PUBLICATIONS

Hao, et al., Real-Time Monitoring of Insulin Using a Graphene Field-Effect Transistor Aptameric Nanosensor, ACS, Applied Materials and Interfaces, 27504-27511, Aug. 3, 2017.
(Continued)

*Primary Examiner* — Amy He
(74) *Attorney, Agent, or Firm* — Aliki K. Collins; AKC Patents, LLC

(57) ABSTRACT

The present disclosure provides a three-dimensional hydrogel-graphene-based biosensor and a preparation method thereof, belonging to the technical field of biosensors. The present disclosure provides a three-dimensional hydrogel-graphene-based biosensor, including a substrate, an electrode layer, a graphene film, and a three-dimensional hydrogel material layer that are stacked in sequence; where the three-dimensional hydrogel material layer is formed of a hydrogel material having a three-dimensional network structure; the hydrogel material is obtained by polymerization of raw materials including an acrylamide monomer and a modified probe molecule; and the modified probe molecule is a probe molecule modified with an acrylamide group. The
(Continued)

three-dimensional hydrogel-graphene-based biosensor has a desirable stability and a high sensitivity.

20 Claims, 5 Drawing Sheets

(51) Int. Cl.
    *C08F 220/56* (2006.01)
    *G01N 33/543* (2006.01)
    *G01N 33/48* (2006.01)
    *G01N 27/02* (2006.01)
    *G01N 33/50* (2006.01)
    *G01N 27/327* (2006.01)
    *G01N 33/68* (2006.01)

(52) U.S. Cl.
    CPC .......... *G01N 27/327* (2013.01); *G01N 33/48* (2013.01); *G01N 33/50* (2013.01); *G01N 33/5438* (2013.01); *C01B 2204/02* (2013.01); *C01B 2204/22* (2013.01); *G01N 33/6887* (2013.01)

(58) Field of Classification Search
CPC .. G01N 33/6887; G01N 27/327; G01N 27/12; G01N 27/414; G01N 27/4145; C01B 32/194; C01B 2204/02; C01B 2204/22; C08F 220/56
See application file for complete search history.

(56) References Cited

FOREIGN PATENT DOCUMENTS

| | | |
|---|---|---|
| CN | 110699431 A | 1/2020 |
| CN | 110776652 A | 2/2020 |
| CN | 112394100 A | 2/2020 |
| DE | 102005017522 A1 | 10/2006 |

OTHER PUBLICATIONS

ISR, PCT/CN2021/103609; dated Jun. 30, 2021.

* cited by examiner

THREE-DIMENSIONAL HYDROGEL-GRAPHENE-BASED BIOSENSOR AND PREPARATION METHOD THEREOF

CROSS REFERENCE TO RELATED APPLICATION

The present application is a continuation and claims the priority and benefit of PCT Patent Application No. PCT/CN2021/103609, entitled "THREE-DIMENSIONAL HYDROGEL-GRAPHENE-BASED BIOSENSOR AND PREPARATION METHOD THEREOF", filed on Jun. 30, 2021, the contents of which are incorporated herein by reference in its entirety.

The present application also claims the benefit and priority of Chinese Patent Application No. CN202110672440.1, entitled "THREE-DIMENSIONAL HYDROGEL-GRAPHENE-BASED BIOSENSOR AND PREPARATION METHOD THEREOF", filed with China National Intellectual Property Administration (CNIPA) on Jun. 17, 2021, the contents of which are incorporated herein by reference in its entirety.

TECHNICAL FIELD

The present disclosure relates to the technical field of biosensors, in particular to a three-dimensional hydrogel-graphene-based biosensor and a preparation method thereof.

BACKGROUND ART

Graphene-based electrical sensors have rapid response and high sensitivity, and can be used combined with probe molecules capable of recognizing target substances with a high specificity, such as aptamers, antibodies and enzymes, to form graphene-based nano-biosensors with an important value for use in the field of disease marker detection.

The graphene-based nano-biosensors reported in existing researches are surface-affinity sensors (DOI: 10.1021/acsami.7b07684). That is, a probe molecule is anchored on a graphene surface through a linking molecule containing an aromatic ring structure, and weakly-charged marker molecules in a solution to be tested captured by the probe molecule may affect the number of mobile carriers per unit cross-sectional area inside the graphene under the action of "electrostatic induction". By measuring changes in the number of mobile carriers, namely changes in a conductivity of the graphene (changes in a current across the graphene), concentration changes can be determined in the marker molecule. During the whole process of detection with the surface-affinity sensor, the graphene surface is always exposed to the solution to be tested. However, actual biological solution samples, such as blood, sweat, and saliva, include many non-target biological macromolecules or impurities. These substances are easy to form biofouling on the graphene surface, affecting the stability and sensitivity of sensor, and even causing sensor failure.

SUMMARY

An objective of the present disclosure is to provide a three-dimensional hydrogel-graphene-based biosensor and a preparation method thereof. The three-dimensional hydrogel-graphene-based biosensor has a desirable stability and a high sensitivity.

To achieve the above objective, the present disclosure provides the following technical solutions.

The present disclosure provides a three-dimensional hydrogel-graphene-based biosensor, including a substrate, an electrode layer, a graphene film, and a three-dimensional hydrogel material layer that are stacked in sequence; where the three-dimensional hydrogel material layer is formed of a hydrogel material having a three-dimensional network structure; the hydrogel material is obtained by polymerization of raw materials including an acrylamide monomer and a modified probe molecule; and the modified probe molecule is a probe molecule modified with an acrylamide group.

Preferably, the hydrogel material may have a pore size of 1.8 μm to 2.2 μm.

Preferably, the three-dimensional hydrogel material layer may have a thickness of 0.63 mm to 2.35 mm.

Preferably, the acrylamide monomer may include acrylamide and bis-acrylamide at a mass ratio of (45-55):1.

Preferably, a mass of the acrylamide monomer and a mole of the modified probe molecule may have a ratio of (5-20) g:1 μmol.

Preferably, the probe molecule may be an aptamer.

Preferably, the modified probe molecule may be a single-stranded DNA containing the acrylamide group at a 5'-end or an RNA containing the acrylamide group at a 5'-end.

Preferably, the graphene film may be formed from monolayer graphene.

Preferably, the electrode layer may include two electrodes arranged in parallel; and the graphene film may be arranged on a surface of each of the two electrodes and a surface of the exposed substrate.

Preferably, the electrode may be a metal electrode.

Preferably, the electrode may be a gold/chromium composite conductive electrode, and may include a chromium layer and a gold layer that are stacked; and the chromium layer may be in contact with the substrate.

Preferably, the substrate may be a flexible substrate or a rigid substrate.

Preferably, the substrate may be a silicon wafer coated with a $SiO_2$ layer on a surface.

The present disclosure further provides a preparation method of the three-dimensional hydrogel-graphene-based biosensor, including the following steps:

preparing the electrode layer on one side of the substrate to obtain a substrate-electrode layer device;

providing the graphene film on a surface of the electrode layer in the substrate-electrode layer device to obtain a substrate-electrode layer-graphene film device; and subjecting a reaction solution to in-situ polymerization on a surface of the graphene film in the substrate-electrode layer-graphene film device, to form a three-dimensional hydrogel material layer on the surface of the graphene film, to obtain the three-dimensional hydrogel-graphene-based biosensor; where the reaction solution includes the acrylamide monomer, the modified probe molecule, an initiator, sodium nitrate, and a solvent.

Preferably, a method for preparing the electrode layer on one side of the substrate may include an electron beam evaporation method.

Preferably, a method for providing the graphene film on a surface of the electrode layer in the substrate-electrode layer device may include the following step:

transferring the graphene film to the surface of the electrode layer by a wetting transfer method.

Preferably, the reaction solution may be obtained by mixing an original colloidal solution, a modified probe molecule solution, and an initiator solution; the original colloidal solution may have 10 wt % to 20 wt % of the acrylamide monomer by mass fraction; the modified probe molecule solution may have a concentration of 8 μmol/L to 12 μmol/L; the initiator may include ammonium persulfate and tetramethylethylenediamine with a dosage ratio of 2 mg:(0.8-1.2) μL, and the initiator solution may have 0.08 mg/μL to 0.12 mg/μL of the ammonium persulfate by concentration; and the original colloidal solution, the modified probe molecule solution, and the initiator solution in the reaction solution may have a volume ratio of 20:(25-35):(3-5).

Preferably, the original colloidal solution may be obtained by diluting an acrylamide monomer mother liquor with a sodium nitrate solution; the acrylamide monomer mother liquor may have 35 wt % to 45 wt % of the acrylamide monomer by mass fraction, and the sodium nitrate solution may have 1.8 μmol/L to 2.2 μmol/L of the sodium nitrate by concentration.

Preferably, a solvent in the acrylamide monomer mother liquor may be water; and a solvent in the sodium nitrate solution may be a Tris-$HNO_3$ buffer.

Preferably, a solvent of the initiator solution may be water.

Preferably, a solvent of the modified probe molecule solution may be phosphate-buffered saline (PBS).

Preferably, the in-situ polymerization may be conducted at room temperature for 10 min to 20 min.

The present disclosure provides a three-dimensional hydrogel-graphene-based biosensor, including a substrate, an electrode layer, a graphene film, and a three-dimensional hydrogel material layer that are stacked in sequence; where the three-dimensional hydrogel material layer is formed of a hydrogel material having a three-dimensional network structure; the hydrogel material is obtained by polymerization of raw materials including an acrylamide monomer and a modified probe molecule; and the modified probe molecule is a probe molecule modified with an acrylamide group.

In the present disclosure, in the three-dimensional hydrogel-graphene-based biosensor, the graphene film is a conductive channel, and the hydrogel material has a three-dimensional network structure, such that target molecules in a solution to be tested can be combined with the probe molecule through meshes. Meanwhile, when using the three-dimensional hydrogel-graphene-based biosensor to measure an actual biological solution sample, an entire hydrogel-probe structure forms an electric double layer on a surface of the graphene conductive channel; when the probe molecule captures the target molecules, a capacitance of the entire electric double layer may change correspondingly with a change in a concentration of the captured target molecules, such that the number of freely-moving electrons inside the graphene changes, thereby changing an electrical conductivity of the graphene. That is, a transfer characteristic curve and Dirac points of the graphene shift with different concentrations of the target molecules to generate detection signals. In the present disclosure, the hydrogel material has a nano-scale three-dimensional network structure, like forming a filter screen on a surface of the graphene film. Therefore, macromolecular substances or impurities in the actual biological solution sample can be effectively blocked outside the hydrogel material, realizing the isolation of non-target molecules in the solution to be tested and the graphene conductive channel, to prevent formation of biofouling on the surface of the graphene film. In addition, target small molecules are made close to the surface of the graphene film along with the solution through interconnected meshes in the hydrogel material, to effectively detect and improve stability and sensitivity of the sensor.

In the present disclosure, a distance between an equivalent charge center of the captured charged target molecules and the graphene film is further adjusted by adjusting a thickness of the three-dimensional hydrogel material layer. Thus, an "electrostatic induction effect" is affected to adjust a sensitivity of the sensor, thereby eventually adjusting a detection range of the target molecules. The results of examples show that when the target molecule is cardiac troponin I (cTn I), a sensor with a three-dimensional hydrogel material layer in a thickness of 0.63 mm to 2.35 mm has a target molecule detection range of 5 aM to 50 nM.

The present disclosure further provides a preparation method of the three-dimensional hydrogel-graphene-based biosensor, including the following steps: preparing the electrode layer on one side of the substrate to obtain a substrate-electrode layer device; providing the graphene film on a surface of the electrode layer in the substrate-electrode layer device to obtain a substrate-electrode layer-graphene film device; and subjecting a reaction solution to in-situ polymerization on a surface of the graphene film in the substrate-electrode layer-graphene film device, to form a three-dimensional hydrogel material layer on the surface of the graphene film, to obtain the three-dimensional hydrogel-graphene-based biosensor; where the reaction solution includes the acrylamide monomer, the modified probe molecule, an initiator, sodium nitrate, and a solvent. In the three-dimensional hydrogel-graphene-based biosensor prepared by the preparation method, the hydrogel material layer and the graphene film are immobilized together through intermolecular force contact. Moreover, different from a probe molecule modification method of traditional surface-based sensors, the probe molecule in the sensor of the present disclosure is modified and immobilized in the hydrogel material. Therefore, when the sensor is used, the hydrogel material can be manually torn off (when the hydrogel material is torn off, the graphene film is not removed; because the graphene film is adhered to the substrate mainly depending on intermolecular interaction, which is far greater than a binding force between the graphene film and the hydrogel material), and may not leave traces of use on the surface of the graphene film, which facilitates reuse of the sensor by re-preparing the hydrogel material layer. Furthermore, after reprocessing, the sensitive material graphene film used twice before and after is not replaced (due to different production batches and human interference during processing, there are differences in electrical signals between different graphene-based devices, which is inconvenient for calibration). Therefore, electrical signals of the sensor do not change, facilitating the calibration of the sensor.

DETAILED DESCRIPTION OF THE EMBODIMENTS

Figure 1:
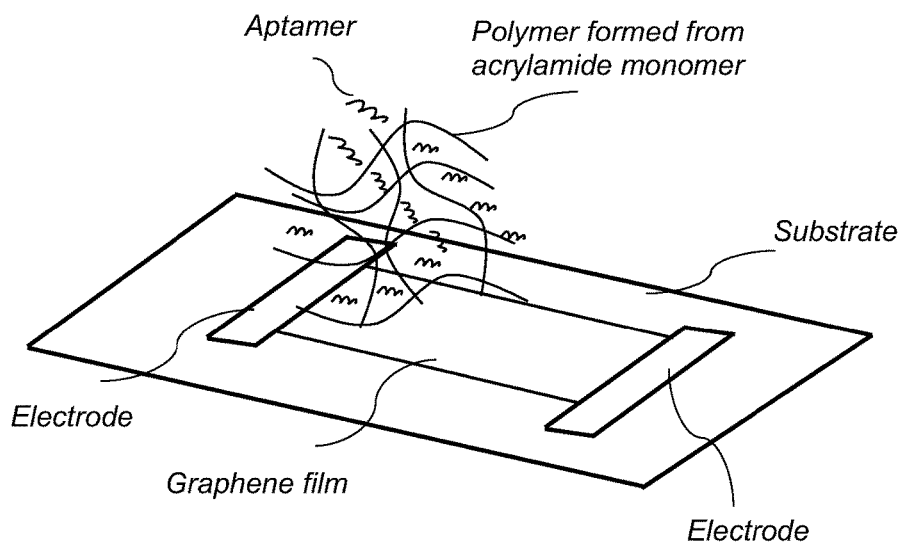
FIG. 1 shows a structural schematic diagram of a three-dimensional hydrogel-graphene-based biosensor provided by the present disclosure.

The present disclosure is further described below with reference to the accompanying drawings and examples.

The present disclosure provides a three-dimensional hydrogel-graphene-based biosensor, including a substrate, an electrode layer, a graphene film, and a three-dimensional hydrogel material layer that are stacked in sequence; where the three-dimensional hydrogel material layer is formed of a hydrogel material having a three-dimensional network structure; the hydrogel material is obtained by polymerization of raw materials including an acrylamide monomer and a modified probe molecule; and the modified probe molecule is a probe molecule modified with an acrylamide group.

In the present disclosure, the three-dimensional hydrogel-graphene-based biosensor includes a substrate. There is no special limitation on the substrate, and any substrates well-known to those skilled in the art can be used; specifically, a flexible substrate or a rigid substrate is available. In an example, the substrate is preferably a silicon wafer coated with a $SiO_2$ layer on a surface, the $SiO_2$ layer has a thickness of preferably 285 nm, and the substrate has a total thickness of preferably 500 μm.

In the present disclosure, the three-dimensional hydrogel-graphene-based biosensor includes an electrode layer stacked on one side of the substrate. In an example, the silicon wafer coated with the $SiO_2$ layer is used as the substrate, and the electrode layer is specifically arranged on a surface of the $SiO_2$ layer. The electrode layer includes preferably two electrodes arranged in parallel; specifically, the two electrodes are arranged at opposite ends of the substrate. The electrode is preferably a metal electrode, more preferably a gold/chromium composite conductive electrode; the gold/chromium composite conductive electrode includes specifically a chromium layer and a gold layer that are stacked, the chromium layer has a thickness of preferably 2 nm, and the gold layer has a thickness of preferably 43 nm; specifically, the chromium layer of the gold/chromium composite conductive electrode is brought into contact with the substrate.

In the present disclosure, the three-dimensional hydrogel-graphene-based biosensor includes a graphene film stacked on a surface of the electrode layer. When the electrode layer includes two electrodes arranged in parallel, the graphene film is arranged on a surface of each of the two electrodes and a surface of the exposed substrate. The graphene film is formed preferably from monolayer graphene.

In the present disclosure, the three-dimensional hydrogel-graphene-based biosensor includes a three-dimensional hydrogel material layer stacked on a surface of the graphene film; the three-dimensional hydrogel material layer is formed of a hydrogel material with a three-dimensional network structure; the hydrogel material is obtained by polymerization of raw materials including an acrylamide monomer and a modified probe molecule; and the modified probe molecule is a probe molecule modified with an acrylamide group. The hydrogel material has a pore diameter of preferably 1.8 μm to 2.2 μm, more preferably 2 μm. The three-dimensional hydrogel material layer has a thickness of preferably 0.63 mm to 2.35 mm. The acrylamide monomer includes preferably acrylamide and bis-acrylamide at a mass ratio of preferably (45-55):1, more preferably 49:1. A mass of the acrylamide monomer and a mole of the modified probe molecule have a ratio of preferably (5-20) g:1 μmol, more preferably (8-12) g:1 μmol. The probe molecule is preferably an aptamer; and the modified probe molecule is preferably a single-stranded DNA containing the acrylamide group at a 5'-end or an RNA containing the acrylamide group at a 5'-end.

The present disclosure further provides a preparation method of the three-dimensional hydrogel-graphene-based biosensor, including the following steps:

preparing the electrode layer on one side of the substrate to obtain a substrate-electrode layer device;

providing the graphene film on a surface of the electrode layer in the substrate-electrode layer device to obtain a substrate-electrode layer-graphene film device; and subjecting a reaction solution to in-situ polymerization on a surface of the graphene film in the substrate-electrode layer-graphene film device, to form a three-dimensional hydrogel material layer on the surface of the graphene film, to obtain the three-dimensional hydrogel-graphene-based biosensor; where the reaction solution includes the acrylamide monomer, the modified probe molecule with the acrylamide group, an initiator, sodium nitrate, and a solvent.

In the present disclosure, unless otherwise specified, all raw materials required for preparation are commercially available products well known to persons skilled in the art.

In the present disclosure, the electrode layer is prepared on one side of the substrate to obtain the substrate-electrode layer device. There is no special limitation on a preparation method of the electrode layer, and methods well known to those skilled in the art can be used; preferably, the electrode layer is prepared by an electron beam evaporation method; there is no special limitation on operating conditions of the electron beam evaporation method, as long as an electrode layer that meets the thickness requirements is obtained.

In the present disclosure, the graphene film is provided on a surface of the electrode layer in the substrate-electrode layer device to obtain the substrate-electrode layer-graphene film device. A method for providing the graphene film on the surface of the electrode layer in the substrate-electrode layer device includes preferably the following step:

transferring the graphene film to the surface of the electrode layer by a wetting transfer method.

In the present disclosure, the graphene film is preferably prepared by chemical vapor deposition; the graphene film is preferably deposited on a surface of a copper foil, that is, front and back sides of the copper foil are deposited with the graphene film, and a single side (referred to as the front side) of the copper foil attached with the graphene film is provided with a polymethyl methacrylate (PMMA) protective layer; in an example, the copper foil (referred to as a composite) containing the graphene film and the PMMA protective layer is a commercially-available.

Figure 2:
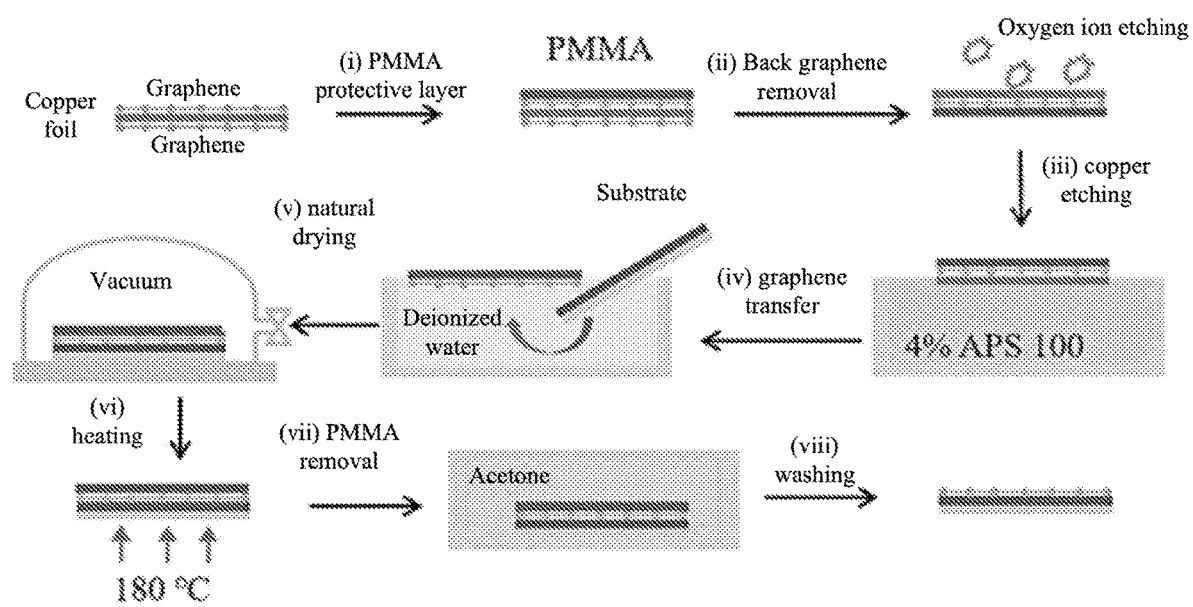
FIG. 2 shows a flow chart of transferring a graphene film to a surface of an electrode layer by a wetting transfer method in the present disclosure.

FIG. 2 shows a flow chart of transferring a graphene film to a surface of an electrode layer by a wetting transfer method in an example of the present disclosure; and the wetting transfer method is described in detail below with reference to FIG. 2. Specifically, the wetting transfer method preferably includes: cutting the composite into a square with a size of 3×3 mm$^2$, and removing the graphene film on the back of the copper foil by oxygen ion etching; putting the copper foil face up (the side with the PMMA protective layer being facing up), to float in an APS 100 copper etching solution with a concentration of 4 wt %, and allowing to stand for 3 h, such that the copper foil is completely etched away, to obtain a graphene film-PMMA protective layer material floating on a surface of the APS 100 copper etching solution; taking out the material by a cover glass and putting into a petri dish filled with deionized water, such that the graphene film of the graphene film-PMMA protective layer material is in contact with the deionized water, and allowing to stand for 15 min to remove the residual APS 100 copper etching solution on the graphene film; this is recorded as 1 washing step; repeating the washing step 2 to 3 times to ensure that residual impurities on the surface of the graphene film are fully removed, to avoid the presence of precipitated crystalline particles between the graphene film and the electrode after moisture evaporation; after the washing, immersing the substrate-electrode layer device in a petri dish, aligning the graphene film floating in the deionized water with a center of the electrode, taking out the graphene film-PMMA protective layer material, and putting in a vacuum box after being naturally dried, and vacuum drying at 25° C. for 5 h, and then heating on a hot plate at 180° C. for 1 h to soften the PMMA protective layer, which in turn makes the contact between the graphene film, the substrate and the electrode more firm; soaking an obtained device in acetone for 1 h to completely remove the PMMA protective layer on the surface of the graphene film, followed by washing with isopropyl alcohol (IPA) and the deionized water, and air-drying with nitrogen to obtain the substrate-electrode layer-graphene film device.

In the present disclosure, a reaction solution is subjected to in-situ polymerization on a surface of the graphene film in the substrate-electrode layer-graphene film device, to form a three-dimensional hydrogel material layer on the surface of the graphene film, to obtain the three-dimensional hydrogel-graphene-based biosensor. The reaction solution includes the acrylamide monomer, the modified probe molecule, an initiator, sodium nitrate, and a solvent. The initiator includes preferably ammonium persulfate (APS) and tetramethylethylenediamine (TEMED) with a dosage ratio of preferably 2 mg:(0.8-1.2) μL, more preferably 2 mg:1 μL. The reaction solution is preferably obtained by mixing an original colloidal solution, a modified probe molecule solution, and an initiator solution. The original colloidal solution has preferably 10 wt % to 20 wt %, more preferably 14 wt % to 17 wt %, and further more preferably 15 wt % to 16 wt % of the acrylamide monomer by mass fraction. The original colloidal solution is preferably obtained by diluting an acrylamide monomer mother liquor with a sodium nitrate solution; the acrylamide monomer mother liquor has preferably 35 wt % to 45 wt %, more preferably 38 wt % to 42 wt %, and further more preferably 39 wt % to 40 wt % of the acrylamide monomer by mass fraction, and a solvent in the acrylamide monomer mother liquor is preferably water; the sodium nitrate solution has preferably 1.8 mol/L to 2.2 mol/L, more preferably 2 mol/L of the sodium nitrate by concentration; and a solvent in the sodium nitrate solution is preferably a Tris-HNO$_3$ buffer, and the Tris-HNO$_3$ buffer has a concentration of preferably 0.5 mol/L and a pH value of preferably 8. The modified probe molecule solution has a concentration of preferably 8 μM to 12 μM, more preferably 10 μM; and a solvent of the modified probe molecule solution is preferably PBS, with a pH value of preferably 7.4. The initiator solution has preferably 0.08 mg/μL to 0.12 mg/μL, more preferably 0.10 mg/μL of the ammonium persulfate by concentration; and a solvent of the initiator solution is preferably water. The original colloidal solution, the modified probe molecule solution, and the initiator solution in the reaction solution have a volume ratio of preferably 20:(25-35):(3-5), more preferably 20:30:4. Preferably, the original colloidal solution and the modified probe molecule solution are mixed, and a resulting mixed solution is mixed with the initiator solution.

In the present disclosure, preferably a bottomless reaction vessel is placed on the surface of the graphene film in the substrate-electrode layer-graphene film device, and the substrate-electrode layer-graphene film device and the reaction vessel are used as molds to prepare the hydrogel material, thereby forming the three-dimensional hydrogel material layer on the surface of the graphene film in the substrate-electrode layer-graphene film device. There is no special limitation on a shape and a size of the reaction vessel, which can be selected according to a shape and a size of the three-dimensional hydrogel material layer; in an example, a reaction vessel with a diameter of 5 mm is specifically used. The reaction vessel is preferably made of polydimethylsiloxane (PDMS).

In the present disclosure, a reaction solution is preferably prepared in the bottomless reaction vessel on the surface of the graphene film in the substrate-electrode layer-graphene film device, and the reaction solution is subjected to in-situ polymerization in the reaction vessel, to form the three-dimensional hydrogel material layer on the surface of the graphene film, to obtain the three-dimensional hydrogel-graphene-based biosensor. There is no special limitation on a dosage of the reaction solution, which can be selected according to an actual required size of the three-dimensional hydrogel material layer. The in-situ polymerization is conducted preferably at room temperature, without additional heating or cooling; in an example, specifically the in-situ polymerization is conducted at 25° C. for preferably 10 min to 20 min, more preferably 15 min. The in-situ polymerization is conducted preferably standing. During the in-situ polymerization, under the action of initiator, the acrylamide monomer and the modified probe molecule form the three-dimensional hydrogel material on the surface of the graphene film through free radical polymerization.

In the present disclosure, after the in-situ polymerization, the reaction vessel is removed to obtain the three-dimensional hydrogel-graphene-based biosensor.

The technical solutions in the present disclosure are clearly and completely described below in conjunction with examples of the present disclosure. It is clear that the described examples are merely a part, rather than all of the examples of the present disclosure. All other examples obtained by a person of ordinary skill in the art based on the examples of the present disclosure without creative efforts shall fall within the protection scope of the present disclosure.

Example 1

FIG. 1 showed a structural schematic diagram of a three-dimensional hydrogel-graphene-based biosensor in the example. The three-dimensional hydrogel-graphene-based biosensor included a substrate, an electrode layer, a graphene film, and a three-dimensional hydrogel material layer that were stacked in sequence; the substrate was a silicon wafer coated with a SiO$_2$ layer, the substrate had a total thickness of 500 μm, and the SiO$_2$ layer had a thickness of 285 nm; the electrode layer included two electrodes arranged in parallel, the electrode was a gold/chromium composite conductive electrode, the gold/chromium composite conductive electrode included a chromium layer and a gold layer that were stacked, and the chromium layer had a thickness of 2 nm, the gold layer had a thickness of 43 nm, specifically the chromium layer of the gold/chromium composite conductive electrode was contacted with the substrate; the graphene film was formed of monolayer graphene; the three-dimensional hydrogel material layer was formed of a hydrogel material with a three-dimensional network structure, the hydrogel material was obtained by polymerization of raw materials including an acrylamide monomer and a modified probe molecule, the modified probe molecule was a probe molecule modified with an acrylamide group, and the three-dimensional hydrogel material layer had a thickness of 1.4 mm; opposite ends of the SiO$_2$ layer on the substrate were provided with the two electrodes, respectively, and the graphene film was provided on a surface of each of the two electrodes and a surface of the exposed substrate.

A preparation method of the three-dimensional hydrogel-graphene-based biosensor included the following steps:

The gold/chromium composite conductive electrodes on the opposite ends of the SiO$_2$ layer were prepared using the silicon wafer (commercially available) coated with the SiO$_2$ layer on the surface as the substrate by an electron beam evaporation method, to obtain a substrate-electrode layer device.

The graphene film was transferred to a surface of the electrode layer by a wetting transfer method; the graphene film was deposited on front and back sides of a copper foil based on a chemical vapor deposition (CVD) method, and a polymethyl methacrylate (PMMA) protective layer was provided on the front side of the copper foil attached with the graphene film (the graphene film-containing composite was commercially available). Specifically, the wetting transfer method preferably included: the composite was cut into a square with a size of 3×3 mm$^2$, and the graphene film was removed on the back of the copper foil by oxygen ion etching; the copper foil was put face up (the side with the PMMA protective layer being facing up), to float in an APS 100 copper etching solution with a concentration of 4 wt %, and allowed to stand for 3 h, such that the copper foil was completely etched away, to obtain a graphene film-PMMA protective layer material floating on a surface of the APS 100 copper etching solution; the material was taken out by a cover glass and put into a petri dish filled with deionized water, such that the graphene film of the graphene film-PMMA protective layer material was in contact with the deionized water, and allowed to stand for 15 min to remove the residual APS 100 copper etching solution on the graphene film; this was recorded as 1 washing step; the washing step repeated 2 to 3 times to ensure that residual impurities on the surface of the graphene film were fully removed, to avoid the presence of precipitated crystalline particles between the graphene film and the electrode after moisture evaporation; after the washing, the substrate-electrode layer device was immersed in a petri dish, the graphene film floating in the deionized water was aligned with a center of the electrode, the graphene film-PMMA protective layer material was taken out, and put in a vacuum box after being naturally dried, and vacuum dried at 25° C. for 5 h, and then heated on a hot plate at 180° C. for 1 h to soften the PMMA protective layer, which in turn made the contact between the graphene film, the substrate and the electrode more firm; an obtained device was soaked in acetone for 1 h to completely remove the PMMA protective layer on the surface of the graphene film, followed by washing with isopropyl alcohol (IPA) and the deionized water, and air-dried with nitrogen to obtain the substrate-electrode layer-graphene film device.

A Tris-HNO$_3$ buffer with a concentration of 0.5 M and a pH value of 8 was prepared using tris(hydroxymethyl)aminomethane (Tris) and nitric acid (HNO$_3$) with deionized water; acrylamide and bis-acrylamide were dissolved in water to obtain a mixed monomer solution, where the acrylamide to the bis-acrylamide in the mixed monomer solution had a mass ratio of 49:1, and the acrylamide and the bis-acrylamide in the mixed monomer solution had a total concentration of 40 wt %; the Tris-HNO$_3$ buffer was mixed with sodium nitrate to obtain a sodium nitrate solution with a sodium nitrate concentration of 2 M, and a total concentration of the acrylamide and the bis-acrylamide was diluted to 16 wt % in the mixed monomer solution using the sodium nitrate solution, to obtain an original colloidal solution; an initiator solution was obtained by dissolving 50 mg of ammonium persulfate (APS) and 25 μL of tetramethylethylenediamine (TEMED) in 500 μL of the deionized water; 20 μL of the original colloidal solution with 30 μL of a 10 μM aptamer solution (a solvent was PBS, pH=7.4) were mixed in a centrifuge tube, where the aptamer was a single-stranded DNA containing an acrylamide group at a 5'-end (purchased from Sangon Biotech (Shanghai) Co., Ltd.); 4 μL of the initiator solution was added into the centrifuge tube, and mixed with the original colloidal solution and the aptamer solution to obtain a reaction solution; a polydimethylsiloxane (PDMS) well with a diameter of 5 mm was fixedly placed on the surface of the graphene film in the substrate-electrode layer-graphene film device, as a reaction vessel; the reaction solution was added to the PDMS well, and a reaction was conducted by standing for 15 min at room temperature (25° C.). The acrylamide, bis-acrylamide and aptamer formed a hydrogel material layer on the surface of the graphene film through free radical polymerization, and the PDMS well was removed to obtain the three-dimensional hydrogel-graphene-based biosensor.

Figure 3:
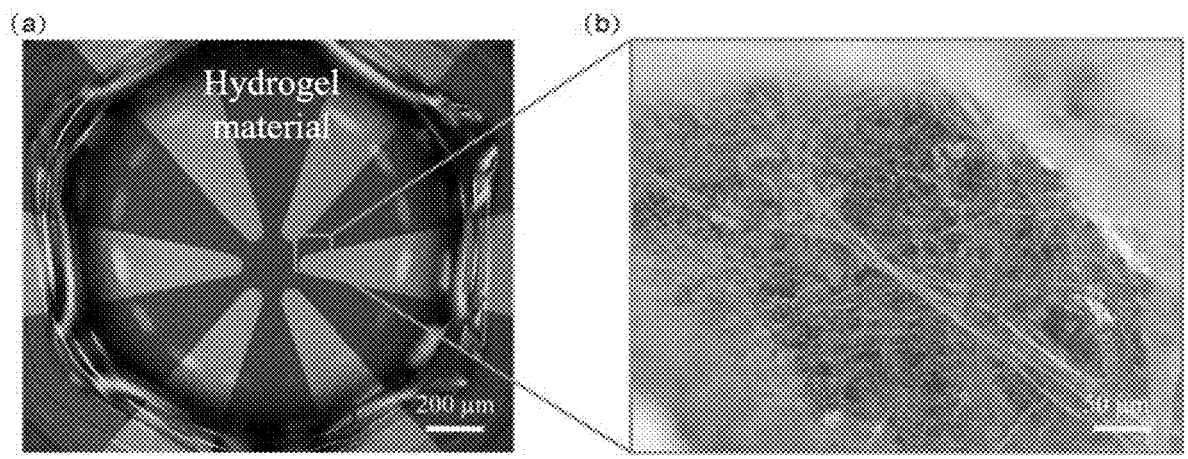
FIG. 3 shows a photo and an optical microscope image of a hydrogel material prepared in Example 1.

FIG. 3 shows a photo and an optical microscope image of the hydrogel material prepared in Example 1, where (a) is the photo of the hydrogel material (a scale bar is 200 μm), and (b) is the optical microscope image of the hydrogel material (a scale bar is 50 μm). It can be seen from FIG. 3 that the hydrogel material prepared by the present disclosure has a porous structure with a pore size of about 2 μm.

Examples 2 to 9

Three-dimensional hydrogel-graphene-based biosensors were prepared with reference to the method in Example 1, except that the thicknesses of the three-dimensional hydrogel material layers were 0.63 mm, 0.78 mm, 1.05 mm, 1.27 mm, 1.6 μmm, 1.73 mm, 1.96 mm, and 2.35 mm, respectively.

Test Example

A performance test of the three-dimensional hydrogel-graphene-based biosensor in the present disclosure included:

1. The cTnI protein solutions were prepared using undiluted sterile rabbit blood (since the undiluted sterile rabbit blood had high viscosity and was easy to coagulate, when preparing each concentration of the cTnI protein solution, the protein was dispersed in the blood as quickly as possible; however, a shaker was strictly forbidden during the preparation to avoid protein inactivation and blood cell disruption), with concentrations of 100 aM, 500 aM, 1 fM, 5 fM, 20 fM, 100 fM, 500 fM, 2 pM, 10 pM, 50 pM, 250 pM and 1000 pM, and stored at 4° C. for later use. Every 8 min, 40 µL of each concentration of the cTnI protein solution was added dropwise to a surface of the hydrogel material layer in each of the three-dimensional hydrogel-graphene-based biosensors prepared in Example 1 using a pipette, and a drain-source voltage and a gate voltage were separately provided using two Keithley 2400 single-channel power workstations, to measure a graphene transfer characteristic curve, respectively; according to the above method, the cTnI protein solution was prepared using serum of the undiluted sterile rabbit blood, and the graphene transfer characteristic curve was measured according to the above method; meanwhile, PBS containing the cTnI protein was used as a control.

The results show that with the increasing concentration of cTnI protein in undiluted blood, the Dirac point moves 61 mV in a negative x-axis direction, which, compared with 64-mV movement of the Dirac point in the negative x-axis direction measured in the PBS, has a rate of change of less than 5%. This result shows that the three-dimensional hydrogel-graphene-based biosensor provided by the present disclosure can accurately identify target molecules and generate response signals in the undiluted blood.

Figure 4:
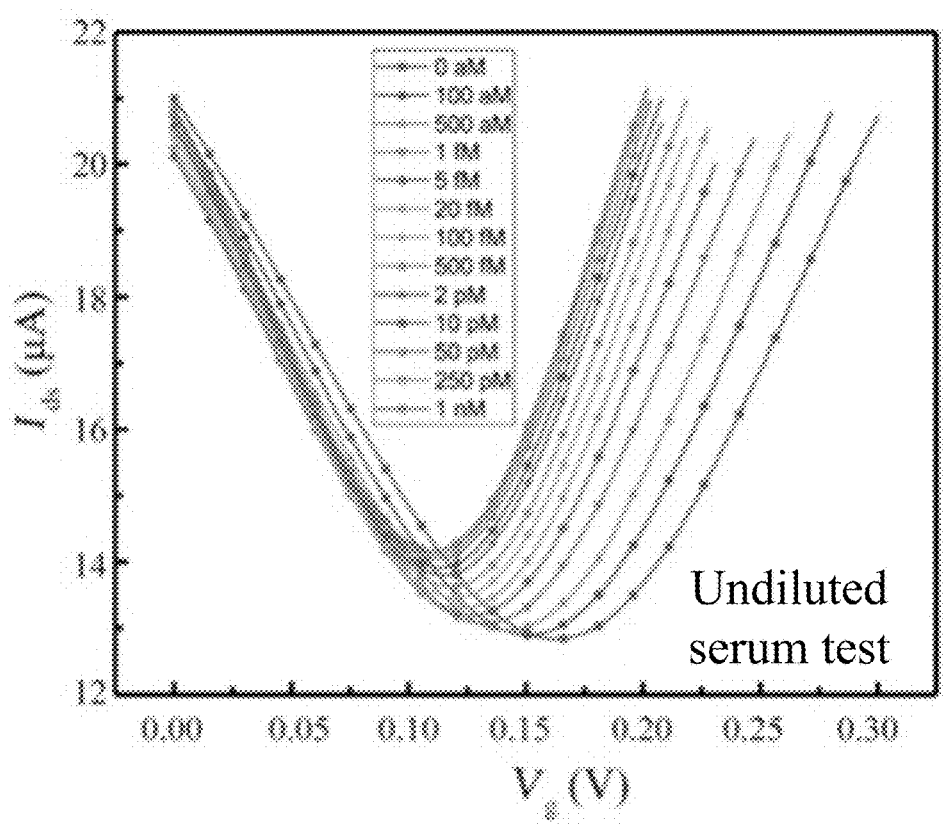
FIG. 4 shows detection signals of a three-dimensional hydrogel-graphene-based biosensor prepared in Example 1 in an undiluted serum.
Figure 5:
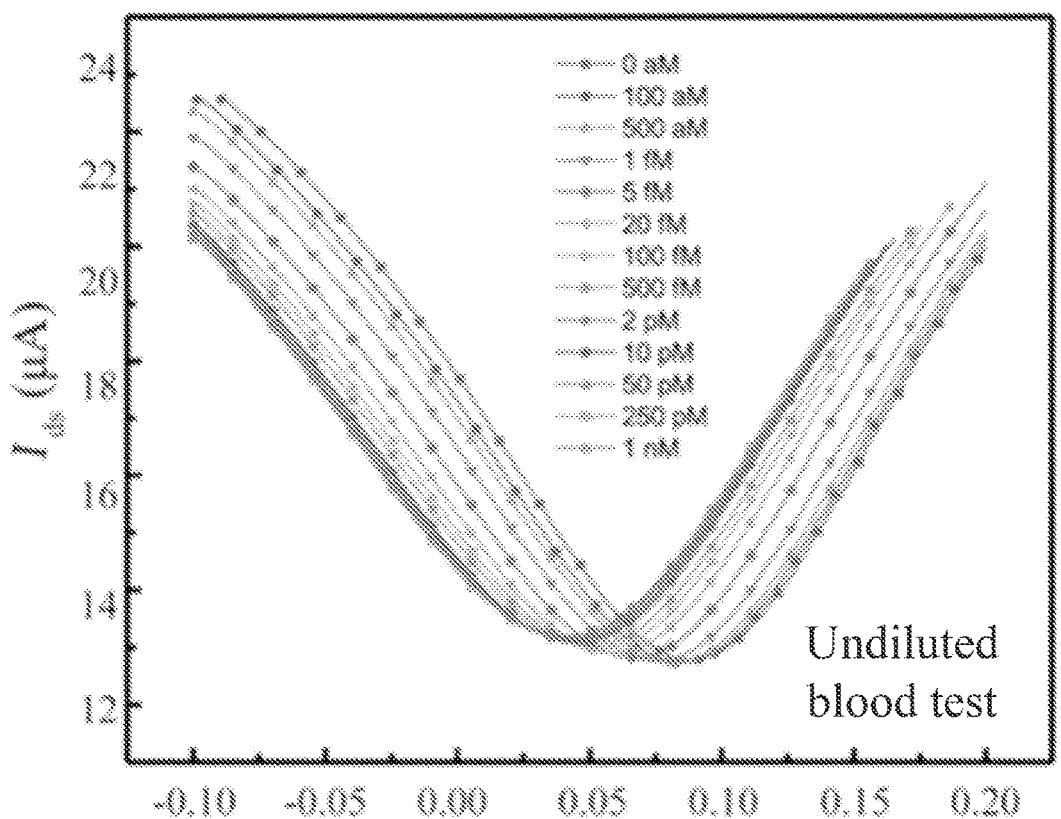
FIG. 5 shows detection signals of the three-dimensional hydrogel-graphene-based biosensor prepared in Example 1 in an undiluted blood.
Figure 6:
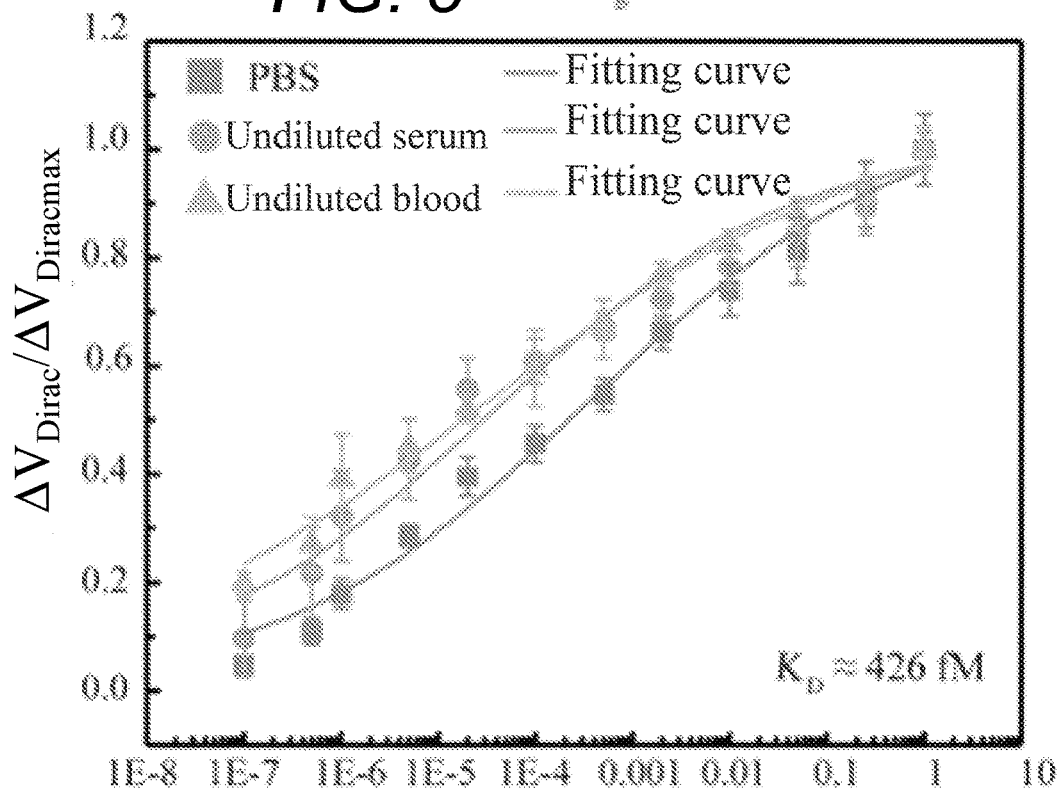
FIG. 6 shows a Hill equation fitting curve based on detection signals of the three-dimensional hydrogel-graphene-based biosensor in the undiluted serum, the undiluted blood and PBS.

FIG. 4 shows detection signals of the three-dimensional hydrogel-graphene-based biosensor prepared in Example 1 in an undiluted serum; FIG. 5 shows detection signals of the three-dimensional hydrogel-graphene-based biosensor prepared in Example 1 in an undiluted blood; FIG. 6 shows a Hill equation fitting curve based on detection signals of the three-dimensional hydrogel-graphene-based biosensor in the undiluted serum, the undiluted blood and the PBS. According to the fitted curve in FIG. 6, a calculated $K_D$ value between the three-dimensional hydrogel-graphene-based biosensor and the cTnI protein in undiluted blood is 426 fM, which has a rate of change of less than 3% and 7% compared to $K_D$ values of 437 fM measured in the PBS and 398 fM measured in the undiluted serum, respectively. In addition, the three-dimensional hydrogel-graphene-based biosensor in undiluted blood has a minimum limit concentration calculated to be 13.9 aM; the data shows a significant improvement even compared with the previously reported sensors that detect cTnI protein in PBS, and a detection limit of the sensor is reduced several to tens of times. The specific comparison data is shown in Table 1.

Table 1 Comparison data of cTnI protein detection between the three-dimensional hydrogel-graphene-based biosensor prepared in Example 1 and other sensing platforms

| Detection method | Material | Detection range | Detection limit |
| --- | --- | --- | --- |
| Electrochemical sensors | Silica nanoparticles | 1 pM to 10 nM | 1 pM[1] |
| Electrochemical immunity Sensor | Gold nanoparticles | 3.9 fM to 3.85 nM | 0.462 fM[2] |
| Microfluidic chip | — | 7.7 pM to 385 nM | 5.7 pM[3] |
| Field effect transistor | Silicon nanowires | 3.5 pM to 1.8 nM | 3.5 pM[4] |
| Electrochemical sensors | Graphene-multilayer carbon nanotubes | 38.5 fM to 385 pM | 36.2 fM[5] |
| Field effect transistor | Hydrogel-graphene | 100 aM to 1 nM | 6.7 aM[Example] |

Note:
in Table 1,
[1]Jo H, Gu H, Jeon W, et al. Electrochemical Aptasensor of Cardiac Troponin I for the Early Diagnosis of Acute Myocardial Infarction [J]. Analytical Chemistry, 2015, 87 (19): 9869-9875.
[2]Zhang L, Xiong C, Wang H, et al. A sensitive electrochemiluminescence immunosensor for cardiac troponin I detection based on dual quenching of the self-enhanced Ru(II) complex by folic acid and in situ generated oxygen [J]. Sensors and Actuators B: Chemical, 2017, 241: 765-772.
[3]Ko S, Kim B, Jo S-S, et al. Electrochemical detection of cardiac troponin I using a microchip with the surface-functionalized poly(dimethylsiloxane) channel [J]. Biosensors & Bioelectronics, 2007, 23 (1): 51-59.
[4]Kong T, Su R, Zhang B, et al. CMOS-compatible, label-free silicon-nanowire biosensors to detect cardiac troponin I for acute myocardial infarction diagnosis [J]. Biosensors & Bioelectronics, 2012, 34 (1): 267-272.
[5]Singal S, Srivastava A K, Dhakate S, et al. Electroactive graphene-multi-walled carbon nanotube hybrid supported impedimetric immunosensor for the detection of human cardiac troponin-I [J]. RSC Advances, 2015, 5 (92): 74994-75003.

Figure 7:
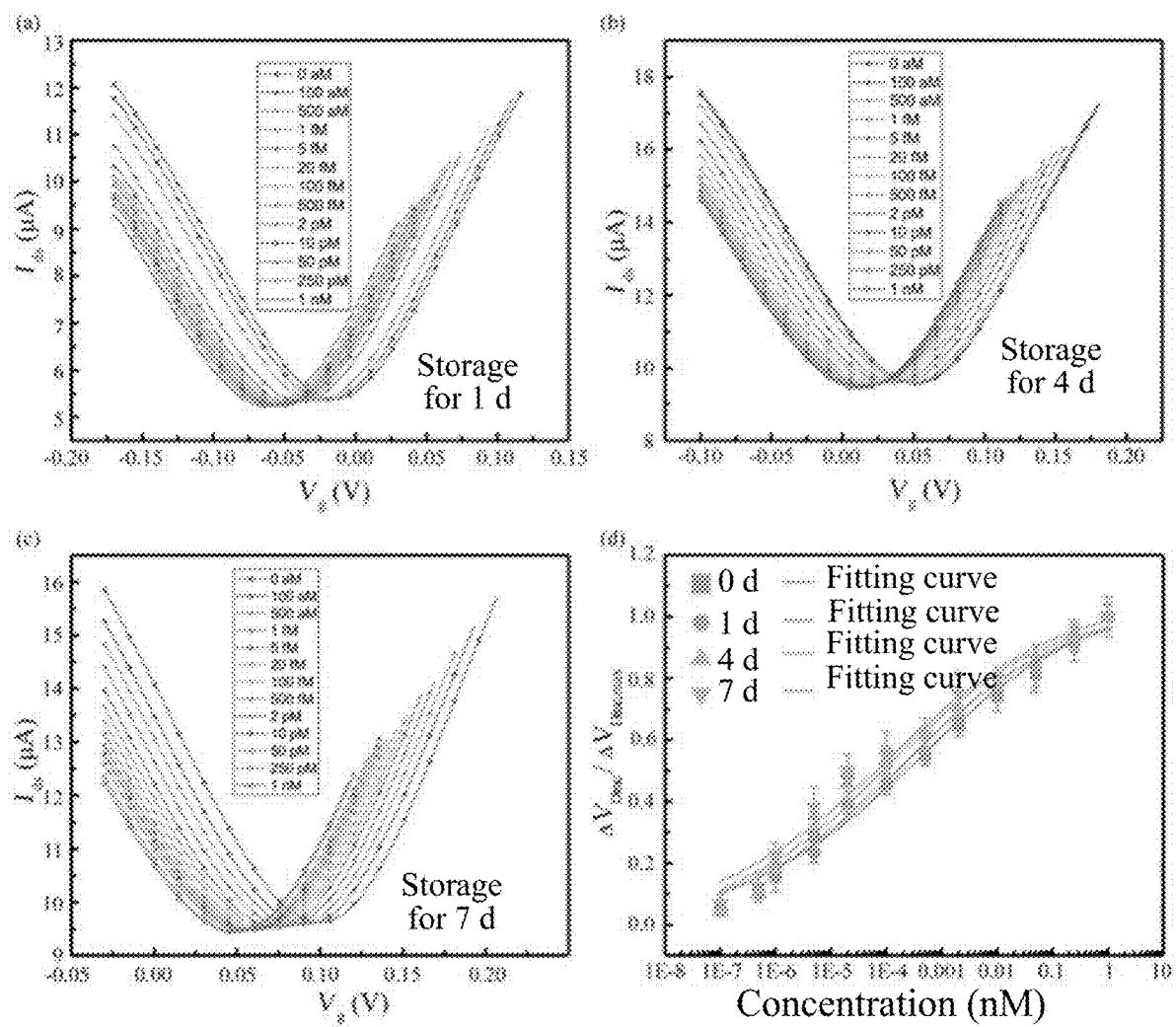
FIG. 7 shows detection signals after placing the three-dimensional hydrogel-graphene-based biosensor prepared in Example 1 at room temperature for different times.

2. The three-dimensional hydrogel-graphene-based biosensor prepared in Example 1 was placed at room temperature for different times, and signals were detected (the target molecule was cTn I). FIG. 7 shows detection signals after placing the three-dimensional hydrogel-graphene-based biosensor prepared in Example 1 at room temperature for different times; where (a) is a detection signal after 1 d, (b) is a detection signal after 4 d, (c) is a detection signal after 7 d, and (d) is a Hill equation fitting curve based on the detection signals after placing the three-dimensional hydrogel-graphene-based biosensor at room temperature for different times. The results show that the transfer characteristic curve of the three-dimensional hydrogel-graphene-based biosensor after being stored at room temperature for 1 d obviously shifts to the negative X-axis direction, with a $\Delta V_{Dirac}$ value decreased significantly by 58 mV. The transfer characteristics curves of the three-dimensional hydrogel-graphene-based biosensor stored at room temperature for 4 d and 7 d show a consistent trend, with $V_{Dirac}$ shifting from 0.055 V to 0.004 V and 0.102 V to 0.046 V, respectively; compared with a response signal $\Delta V_{Dirac}$=64 mV of the three-dimensional hydrogel-graphene-based biosensor used immediately after processing, the change rates are 8% and 12.5%, respectively. This shows that the three-dimensional hydrogel-graphene-based biosensor provided by the present disclosure has desirable stability, and performances of the three-dimensional hydrogel-graphene-based biosensor are not significantly attenuated if being placed for a long time at room temperature.

Figure 8:
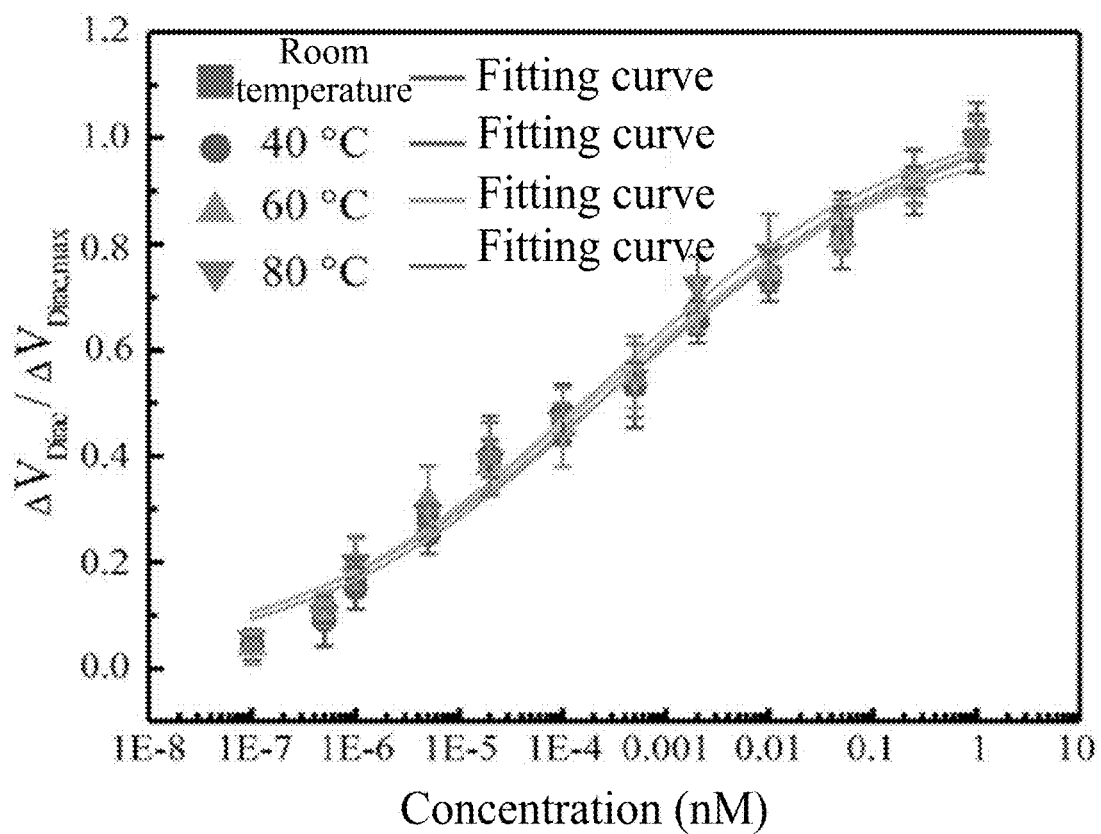
FIG. 8 shows detection signals after placing the three-dimensional hydrogel-graphene-based biosensor prepared in Example 1 under different temperatures for 1 h.

3. The three-dimensional hydrogel-graphene-based biosensor prepared in Example 1 was placed at room temperature, 40° C., 60° C. and 80° C. for 1 h, and signals were detected (the target molecule was cTn I). FIG. 8 shows detection signals after placing the three-dimensional hydrogel-graphene-based biosensor prepared in Example 1 under different temperatures for 1 h. The results show that the three-dimensional hydrogel-graphene-based biosensor provided by the present disclosure has desirable high-temperature resistance, and the detection signal remains stable at 80° C.

Figure 9:
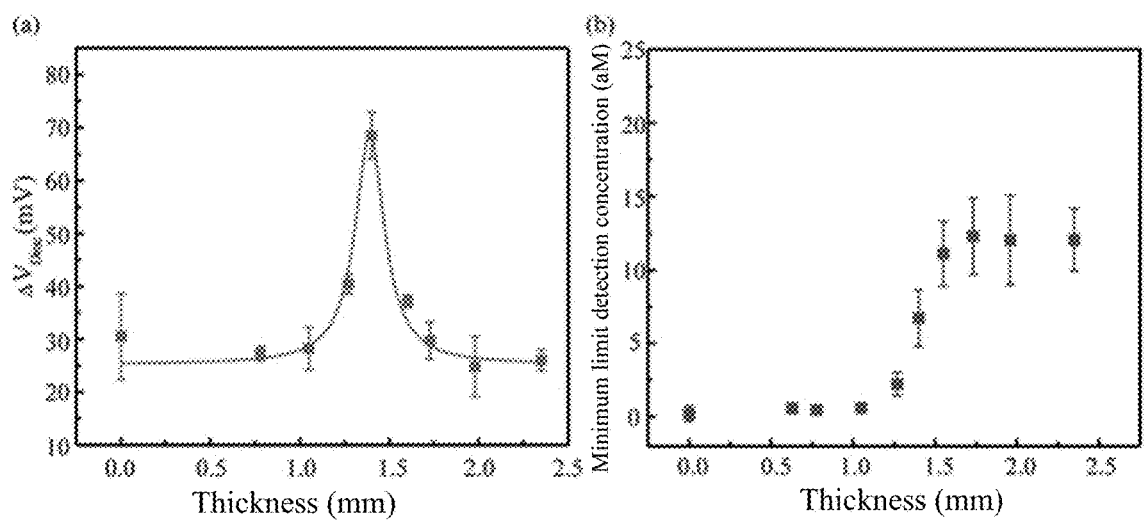
FIG. 9 shows detection signals of three-dimensional hydrogel-graphene-based biosensors with a three-dimensional hydrogel material layer in different thicknesses.

4. The signals were detected for the three-dimensional hydrogel-graphene-based biosensors with a three-dimensional hydrogel material layer in different thicknesses (the thicknesses of the three-dimensional hydrogel material layers were 0.63 mm, 0.78 mm, 1.05 mm, 1.27 mm, 1.4 mm, 1.6 mm, 1.73 mm, 1.96 mm, and 2.35 mm, respectively)

prepared in Examples 1 to 9 (the target molecule was cTn I). FIG. 9 shows detection signals of three-dimensional hydrogel-graphene-based biosensors with a three-dimensional hydrogel material layer in different thicknesses; where (a) is a relationship between a variation of the signal gain Dirac point and a thickness of the three-dimensional hydrogel material layer, and (b) is a relationship between a detection limit and the thickness of the three-dimensional hydrogel material layer. The results show that a distance between an equivalent charge center of the captured charged target molecules and the graphene film is further adjusted by adjusting a thickness of the three-dimensional hydrogel material layer. Thus, an "electrostatic induction effect" is affected to adjust a sensitivity of the sensor, thereby eventually adjusting a detection range of the target molecules.

The above description of examples is merely provided to help illustrate the method of the present disclosure and a core idea thereof. It should be noted that several improvements and modifications may be made by persons of ordinary skill in the art without departing from the principle of the present disclosure, and these improvements and modifications should also fall within the protection scope of the present disclosure. Various amendments to these embodiments are apparent to those of professional skill in the art, and the general principles defined herein may be implemented in other embodiments without departing from the spirit or scope of the present disclosure. Thus, the present disclosure is not limited to the examples shown herein but falls within the widest scope consistent with the principles and novel features disclosed herein.

Several embodiments of the present invention have been described. Nevertheless, it will be understood that various modifications may be made without departing from the spirit and scope of the invention. Accordingly, other embodiments are within the scope of the following claims.

What is claimed is:

1. A three-dimensional hydrogel-graphene-based biosensor, comprising a substrate, an electrode layer, a graphene film, and a three-dimensional hydrogel material layer that are stacked in sequence; wherein the three-dimensional hydrogel material layer is formed of a hydrogel material having a three-dimensional network structure; the hydrogel material is obtained by polymerization of raw materials comprising an acrylamide monomer and a modified probe molecule; and the modified probe molecule is a probe molecule modified with an acrylamide group, wherein the three-dimensional hydrogel material layer has a thickness of 0.63 mm to 2.35 mm.

2. The three-dimensional hydrogel-graphene-based biosensor according to claim 1, wherein the hydrogel material has a pore size of 1.8 µm to 2.2 µm.

3. The three-dimensional hydrogel-graphene-based biosensor according to claim 1, wherein the acrylamide monomer comprises acrylamide and bis-acrylamide at a mass ratio of (45-55):1.

4. The three-dimensional hydrogel-graphene-based biosensor according to claim 3, wherein a mass of the acrylamide monomer and a mole of the modified probe molecule have a ratio of (5-20) g:1 µmol.

5. The three-dimensional hydrogel-graphene-based biosensor according to claim 1, wherein a mass of the acrylamide monomer and a mole of the modified probe molecule have a ratio of (5-20) g:1 µmol.

6. The three-dimensional hydrogel-graphene-based biosensor according to claim 1, wherein the probe molecule is an aptamer.

7. The three-dimensional hydrogel-graphene-based biosensor according to claim 1, wherein the graphene film is formed from monolayer graphene.

8. The three-dimensional hydrogel-graphene-based biosensor according to claim 1, wherein the electrode layer comprises two electrodes arranged in parallel and the graphene film is arranged on a surface of each of the two electrodes and a surface of the exposed substrate.

9. A preparation method of the three-dimensional hydrogel-graphene-based biosensor according to claim 1, comprising the following steps:
preparing the electrode layer on one side of the substrate to obtain a substrate-electrode layer device;
providing the graphene film on a surface of the electrode layer in the substrate-electrode layer device to obtain a substrate-electrode layer-graphene film device; and
subjecting a reaction solution to in-situ polymerization on a surface of the graphene film in the substrate-electrode layer-graphene film device, to form a three-dimensional hydrogel material layer on the surface of the graphene film, to obtain the three-dimensional hydrogel-graphene-based biosensor; wherein the reaction solution comprises the acrylamide monomer, the modified probe molecule, an initiator, sodium nitrate, and a solvent.

10. The preparation method according to claim 9, wherein the hydrogel material has a pore size of 1.8 µm to 2.2 µm.

11. The preparation method according to claim 10, wherein a method for providing the graphene film on a surface of the electrode layer in the substrate-electrode layer device comprises the following step:
transferring the graphene film to the surface of the electrode layer by a wetting transfer method.

12. The preparation method according to claim 9, wherein the acrylamide monomer comprises acrylamide and bis-acrylamide at a mass ratio of (45-55):1.

13. The preparation method according to claim 12, wherein a mass of the acrylamide monomer and a mole of the modified probe molecule have a ratio of (5-20) g:1 µmol.

14. The preparation method according to claim 12, wherein a method for providing the graphene film on a surface of the electrode layer in the substrate-electrode layer device comprises the following step:
transferring the graphene film to the surface of the electrode layer by a wetting transfer method.

15. The preparation method according to claim 9, wherein a mass of the acrylamide monomer and a mole of the modified probe molecule have a ratio of (5-20) g:1 µmol.

16. The preparation method according to claim 15, wherein a method for providing the graphene film on a surface of the electrode layer in the substrate-electrode layer device comprises the following step:
transferring the graphene film to the surface of the electrode layer by a wetting transfer method.

17. The preparation method according to claim 9, wherein the probe molecule is an aptamer.

18. The preparation method according to claim 9, wherein the graphene film is formed from monolayer graphene.

19. The preparation method according to claim 9, wherein the electrode layer comprises two electrodes arranged in parallel; and the graphene film is arranged on a surface of each of the two electrodes and a surface of the exposed substrate.

20. The preparation method according to claim 9, wherein a method for providing the graphene film on a surface of the electrode layer in the substrate-electrode layer device comprises the following step:

transferring the graphene film to the surface of the electrode layer by a wetting transfer method.

\* \* \* \* \*